United States Patent
Böhm et al.

(10) Patent No.: US 6,326,494 B1
(45) Date of Patent: Dec. 4, 2001

(54) 1,7-DIAROXY- OR 1,7-ARYLTHIO-SUBSTITUTED PERYLENE-3,4,9,10-TETRACARBOXYLIC ACIDS, THEIR DIANHYDRIDES AND DIIMIDES

(75) Inventors: Arno Böhm, Mannheim; Harald Arms, Worms; Georg Henning; Peter Blaschka, both of Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/631,291

(22) Filed: Aug. 2, 2000

Related U.S. Application Data

(62) Division of application No. 09/091,262, filed as application No. PCT/EP96/05519 on Dec. 11, 1996, now Pat. No. 6,143,905.

(30) Foreign Application Priority Data

Dec. 18, 1995 (DE) ................................ 195 47 209

(51) Int. Cl.[7] ........................ C07D 31/473; C09B 3/14; C09K 11/06
(52) U.S. Cl. ........................ 546/37; 106/493; 106/499; 252/301.17; 252/301.26; 252/301.35; 8/568
(58) Field of Search ........................ 546/37; 252/301.26, 252/301.35, 301.17; 8/568; 106/493, 499

(56) References Cited

U.S. PATENT DOCUMENTS 5,470,502 * 11/1995 Hahn et al. .................... 252/301.35
5,677,417    10/1997 Muellen et al. .

FOREIGN PATENT DOCUMENTS

| 412122 | 4/1925 | (DE) . |
|---|---|---|
| A 0 055 363 | 7/1982 | (EP) . |
| A 39 912 | 2/1984 | (EP) . |
| A 0 227 980 | 7/1987 | (EP) . |
| WO A 94 25504 | 11/1994 | (WO) . |
| WO A 96 22005 | 7/1996 | (WO) . |
| WO A 96 22331 | 7/1996 | (WO) . |

OTHER PUBLICATIONS

Dyes and Pigments, Bd. 11, Nr. 4, 1989 Barking, Essex, "New Perylene and Violanthrone Dyestuffs for Fluorescent Collectors", PP. 303–317.
Chemical Abstract, vol. 110, No. 3, Jan. 16, 1989, Rogovik, V.I. Et Al., "Chemistry of Peryliene. Halo Derivatives of 3, 4, 9, 10–Perylenetetracarboxylic Acid", pp. 513.
Chemical Abstract, vol. 93, No. 9, Sep. 1, 1980, Rogovik, V.I. Et Al., "Chemistry of Perylene, Ntration of Perylene–3, 4, 9, 10–Tetracarboxylic Acid", pp. 622.
Chemical Abstracts, vol. 69, No. 6, Aug. 9, 1968, Karpukhin, P.P. Et Al.., "Fiber–Reactive Vat Dyes Dervived From the Diimide of Perylenetetracarboxylic Acid", pp. 1932.

* cited by examiner

Primary Examiner—C. S. Aulakh
(74) Attorney, Agent, or Firm—Oblon, Spivak, McClelland, Maier & Neustadt, P.C.

(57) ABSTRACT

A 1,7-disubstituted perylene-3,4,9,10-tetracarboxylic diimide of the general formula VI:

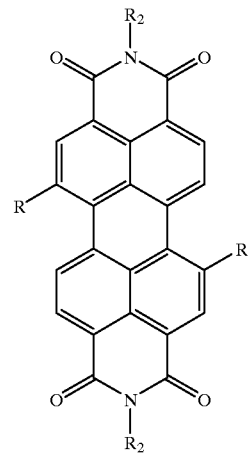

Compositions or products comprising the compound of formula VI. Compositions comprising 1,7-diaroxy- or 1,7-diarylthio-substituted perylene-3,4,9,10-tetracarboxylic dianhydrides (I) or 1,7-diaroxy- or 1,7-diarylthio-substituted perylene-3,4,9,10-tetracarboxylic acids (Ia).

6 Claims, No Drawings

1,7-DIAROXY- OR 1,7-ARYLTHIO-SUBSTITUTED PERYLENE-3,4,9,10-TETRACARBOXYLIC ACIDS, THEIR DIANHYDRIDES AND DIIMIDES

This application is a division of Ser. No. 09/091,262 filed Jun. 18, 1998 now U.S. Pat. No. 6,143,905 which is a 371 of PCT/EP96/05519 filed Dec. 11, 1996.

The present invention relates to novel, 1,7-disubstituted perylene-3,4,9,10-tetracarboxylic dianhydrides of the general formula I and perylene-3,4,9,10-tetracarboxylic acids of the general formula Ia

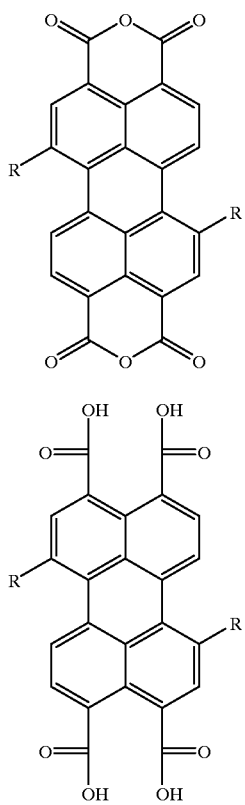

where

R is aryloxy, arylthio, hetaryloxy or hetarylthio each of which can be substituted one or more times by $C_1$–$C_{30}$-alkyl whose carbon chain can be interrupted by one or more groups —O—, —S—, —NR$^1$—, —CO— and/or —SO$_2$— and/or can be substituted one or more times by —COOR$^1$, —SO$_3$R$^1$, hydroxyl, cyano, $C_1$–$C_6$-alkoxy, $C_5$–$C_8$-cycloalkyl or a 5- to 7-membered heterocyclic radical which is attached via nitrogen and can contain further heteroatoms, or can be substituted one or more times by $C_1$–$C_6$-alkoxy, cyano, —COOR$^1$ or —SO$_3$R$^1$, where R$^1$ is hydrogen or $C_1$–$C_6$-alkyl and to a process for the preparation of the perylene-3,4,9,10-tetracarboxylic dianhydrides (I) or of the acids (Ia) and to their use as pigments, laser dyes and precursors for preparing fluorescent dyes, polymeric colorants, pigments and pigment additives.

The invention additionally relates to novel 1,7-disubstituted perylene-3,4,9,10-tetracarboxylic diimides of the general formula

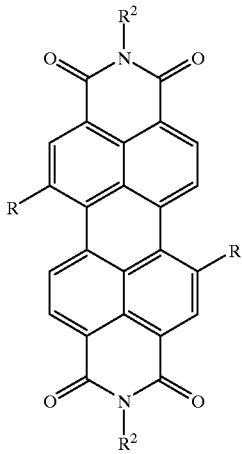

where

R is aryloxy, arylthio, hetaryloxy or hetarylthio each of which can be substituted one or more times by $C_1$–$C_{30}$-alkyl whose carbon chain can be interrupted by one or more groups —O—, —S—, —NR$^1$—, —CO— and/or —SO$_2$— and/or can be substituted one or more times by —COOR$^1$, —SO$_3$R$^1$, hydroxyl, cyano, $C_1$–$C_6$-alkoxy, $C_5$–$C_8$-cycloalkyl or a 5- to 7-membered heterocyclic radical which is attached via nitrogen and can contain further heteroatoms, or can be substituted one or more times by $C_1$–$C_6$-alkoxy, cyano, —COOR$^1$ or —SO$_3$R$^1$, where R$^1$ is hydrogen or $C_1$–$C_6$-alkyl, and R$^2$ is $C_4$–$C_{30}$-alkyl whose carbon chain can be interrupted by one or more groups —O—, —S— or —CO—, or is $C_5$–$C_8$-cycloalkyl or aryl which can be substituted one or more times by $C_1$–$C_6$-alkyl or $C_1$–$C_6$-alkoxy, as intermediates for the perylene-3,4,9,10-tetracarboxylic dianhydrides (I) and the acids (Ia) and to a process for the preparation of the perylene-3,4,9,10-tetracarboxylic diimides (VI).

Perylene-3,4,9,10-tetracarboxylic acids and their anhydrides are known as important intermediates for the preparation of perylimide pigments and perylimide dyes, but are also suitable themselves for coloring, or pigmenting, high molecular mass organic materials.

In addition to unsubstituted perylene-3,4,9,10-tetracarboxylic acid, which can be obtained by hydrolyzing perylene-3,4,9,10-tetracarboxylic diimide in concentrated sulfuric acid at about 200° C., there is particular interest in perylene tetracarboxylic acids which are substituted in the perylene skeleton and whose properties in use, such as solubility, inherent color and fluorescence, can be tailored by introducing suitable substituents.

WO-A-94/25504 discloses 1,6,7,12-tetraaroxy-substituted perylene-3,4,9,10-tetracarboxylic dianhydrides prepared by hydrolyzing the corresponding diumides under alkaline conditions in a polar protic solvent. The tetraaroxy-substituted diimides themselves have been obtained by reacting the tetrachlorinated diimides with arylates (EP-A-227 980).

1,7-disubstituted perylene-3,4,9,10-tetracarboxylic acids such as the novel compounds (Ia), which like all perylene-3,4,9,10-tetracarboxylic acids are generally in the form of the dianhydrides, have not been disclosed to date. Even the dihalogenated perylene-3,4,9,10-tetracarboxylic diimides described in EP-A-39 912 and DRP 412 122 are always mixtures of products with different degrees of halogenation (especially tetra-, tri- and monohalogenated products); it was not possible to prepare specifically the dihalogenated diimides.

It is an object of the invention to provide novel, disubstituted perylene-3,4,9,10-tetracarboxylic acids and dianhydrides.

We have found that this object is achieved by the 1,7-disubstituted perylene-3,4,9,10-tetracarboxylic dianhydrides and the corresponding acids of the formulae I and Ia defined at the outset (referred to below as dianhydrides I).

Preferred dianhydrides I are the subject of the subclaim.

The object has additionally been achieved by a process for the preparation of the dianhydrides I, which comprises a) reacting 1,7-dibromoperylene-3,4,9,10-tetracarboxylic dianhydride (II) or
1,7-dibromoperylene-3,4,9,10-tetracarboxylic acid (IIa), in the presence of a polar aprotic solvent and in the presence or absence of an imidation catalyst, with a primary amine of the general formula III

   III in which $R^2$ is $C_4$–$C_{30}$-alkyl whose carbon chain can be interrupted by one or more groups —O—, —S— or —CO—, or is $C_5$–$C_8$-cycloalkyl or aryl which can be substituted one or more times by $C_1$–$C_6$-alkyl or $C_1$–$C_6$-alkoxy, b) reacting the 1,7-dibromoperylene-3,4,9,10-tetracarboxylic diimides, formed in step a), of the general formula IV

IV

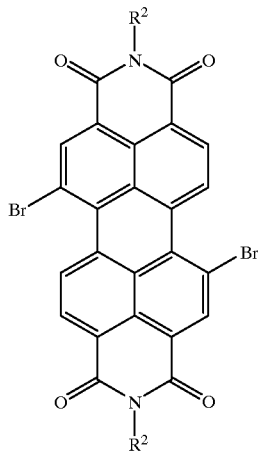

in the presence of an inert aprotic solvent and of a non-nucleophilic or only weakly nucleophilic base with an aromatic alcohol or thioalcohol of the general formula V

   V and hydrolyzing the 1,7-disubstituted perylene-3,4,9,10-tetracarboxylic diimides, formed in step b), of the general formula VI

VI

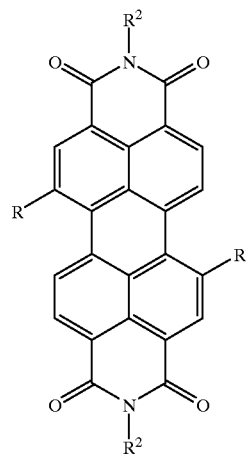

in the presence of a polar protic solvent and a base to give the dianhydrides I.

In addition we have discovered the 1,7-disubstituted perylene-3,4,9,10-tetracarboxylic diimides of the formula VI defined at the outset (referred to below as perylimides VI) as intermediates for the dianhydrides I, and processes for the preparation of the perylimides VI which comprise steps a) and b) of the process for the preparation of the corresponding dianhydrides I.

Preferred perylimides VI are the subject of the subclaim.

We have also found a second process for the preparation of the dianhydrides I, which comprises reacting 1,7-dibromoperylene-3,4,9,10-tetracarboxylic dianhydride (II) or 1,7-dibromoperylene-3,4,9,10-tetracarboxylic acid (IIa) with an aromatic alcohol or thioalcohol of the formula V in the presence of an aprotic solvent and of an inorganic base.

Additionally, we have found a process for the preparation of 1,7-dibromoperylene-3,4,9,10-tetracarboxylic dianhydride (IIa) or 1,7-dibromoperylene-3,4,9,10-tetracarboxylic acid by brominating perylene-3,4,9,10-tetracarboxylic dianhydride or, respectively, perylene-3,4,9,10-tetracarboxylic acid in 100% by weight sulfuric acid, which comprises brominating in the presence of iodine at from 80 to 90° C. and metering in the bromine slowly.

Moreover, we have discovered the use of the dianhydrides I as pigments, laser dyes and precursors for preparing fluorescent dyes, polymeric colorants, pigments and pigment additives.

Finally, we have discovered the use of the perylimides VI as pigments and dyes for coloring high molecular mass organic materials and inorganic materials, as laser dyes and as organic materials for electroluminescence applications.

Suitable unsubstituted radicals R are phenoxy, phenylthio, 2-naphthyloxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio, with phenoxy and 2-naphthyloxy being preferred.

Alkyl substituents of radicals R (and alkyl radicals $R^1$ and $R^2$)) can be either straight-chain or branched.

Specific examples of these substituents (or, respectively, of substituents thereof) are:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial names and derive from the alcohols obtained by oxo synthesis—cf. in this context Ullmanns Encyklopädie der technischen Chemie, 4th Edition, Volume 7, 215–217, and Volume 11, 435 and 436);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 4,7-dithiaoctyl, 4,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-N-methylamino- and 2-(N-ethylamino)ethyl, 2-(N,N-dimethylamino)ethyl, 2- and 3-(N,N-dimethylamino)propyl, 3-isopropylaminopropyl, 2- and 4-(N-propylamino)butyl, 2- and 4-(N,N-dimethylamino)butyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

propan-2-on-1-yl, butan-3-on-1-yl, butan-3-on-2-yl and 2-ethylpentan-3-on-1-yl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

methylcarboxymethyl, ethylcarboxymethyl, propylcarboxymethyl, butylcarboxymethyl, pentylcarboxymethyl, hexylcarboxymethyl, methyl-2-carboxyethyl, ethyl-2-carboxyethyl, propyl-2-carboxyethyl, butyl-2-carboxyethyl, pentyl-2-carboxyethyl, hexyl-2-carboxyethyl, methyl-3-carboxypropyl, ethyl-3-carboxypropyl, propyl-3-carboxypropyl, butyl-3-carboxypropyl, pentyl-3-carboxypropyl, hexyl-3-carboxypropyl, methyl-4-carboxybutyl, methyl-5-carboxypentyl, methyl-6-carboxyhexyl, methyl-8-carboxyoctyl, methyl-10-carboxydecyl, methyl-12-carboxydodecyl and methyl-14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

methylsulfomethyl, ethylsulfomethyl, propylsulfomethyl, butylsulfomethyl, pentylsulfomethyl, hexylsulfomethyl, methyl-2-sulfoethyl, ethyl-2-sulfoethyl, propyl-2-sulfoethyl, butyl-2-sulfoethyl, pentyl-2-sulfoethyl, hexyl-2-sulfoethyl, methyl-3-sulfopropyl, ethyl-3-sulfopropyl, propyl-3-sulfopropyl, butyl-3-sulfopropyl, pentyl-3-sulfopropyl and hexyl-3-sulfopropyl, methyl-4-sulfobutyl, methyl-5-sulfopentyl, methyl-6-sulfohexyl, methyl-8-sulfooctyl, methyl-10-sulfodecyl, methyl-12-sulfododecyl and methyl-14-sulfotetradecyl;

2-hydroxyethyl, 2- and 3-hydroxypropyl, 1-hydroxyprop-2-yl, 2- and 4-hydroxybutyl, 1-hydroxybut-2-yl and 8-hydroxy-4-oxaoctyl, 2-cyanoethyl, 3-cyanopropyl, 2-methyl-3-ethyl-3-cyanopropyl, 7-cyano-7-ethylheptyl and 4-methyl-7-methyl-7-cyanoheptyl;

methoxy, ethoxy, propoxy, isopropoxy, butoxy, isobutoxy, tert-butoxy, pentoxy, isopentoxy, neopentoxy, tert-pentoxy and hexoxy;

cyclopentyl, cyclohexyl, cycloheptyl, cyclooctyl, 2-dioxanyl, 4-morpholinyl, 2- and 3-tetrahydrofuryl, 1-, 2- and 3-pyrrolidinyl and 1-, 2-, 3- and 4-piperidyl.

Examples of suitable radicals $R^1$ are hydrogen and the abovementioned $C_1$–$C_6$-alkyl radicals.

Examples of suitable radicals $R^2$ are the abovementioned $C_4$–$C_{30}$-alkyl radicals, $C_4$–$C_{30}$-alkyl radicals interrupted by —O—, —S— or —CO—, and the $C_5$–$C_8$-cycloalkyl radicals and aryl radicals, for example naphthyl and, in particular, phenyl, which may be substituted by 1, 2 or 3 of the $C_1$–$C_6$-alkyl or $C_1$–$C_6$-alkoxy radicals mentioned, such as 2-, 3- and 4-methylphenyl, 2,4-, 3,5- and 2,6-dimethyiphenyl, 2,4,6-triy,ethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-dfsopropyilphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5 and 2,6-diisobutylphenyl, 2,4,6-triisobutylphenyl, 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl.

The dianhydrides I can be prepared by the novel multistage process in which in step a) 1,7-dibromoperylene-3,4,9,10-tetracarboxylic dianhydride (II) is reacted with a primary amine III to give the corresponding 1,7-dibromoperylene-3,4,9,10-tetracarboxylic diimide IV, which is reacted in step b) with an aromatic alcohol or thioalcohol V to give the perylimide VI, which finally in step c) is hydrolyzed under basic conditions to give the dianhydride I, or by the novel single-stage process, by reacting 1,7-dibromoperylene-3,4,9,10-tetracarboxylic dianhydride (II) directly with the aromatic alcohol or thioalcohol V.

In general, however, the products obtained in the single-stage process variant are more highly contaminated and must therefore be purified subsequently, for example by fractional crystallization or column filtration over silica gel;

for this reason, preference is given to the three-stage process variant in the majority of cases.

1,7-Dibromoperylene-3,4,9,10-tetracarboxylic dianhydride (II), the precursor for the novel preparation process, can be obtained in accordance with the invention by selectively brominating perylene-3,4,9,10-tetracarboxylic dianhydride in 100% by weight sulfuric acid (monohydrate).

The procedure here advantageously comprises first stirring perylene-3,4,9,10-tetracarboxylic dianhydride in sulfuric acid for 2 to 16 h and then heating this mixture to the reaction temperature (generally from 80 to 90° C.) after adding a halogenation catalyst such as iodine (preferably 30–40 mmol per mole of anhydride). Bromine is then added dropwise (usually over 6–10 h), preferably using 2–2.5 mol of bromine ($Br_2$) per mole of anhydride. After cooling to room temperature and displacing the unreacted bromine by nitrogen, the concentration of sulfuric acid is lowered by adding water, a little at a time, to about 85–88% by weight.

Working up the reaction mixture to give 1,7-dibromoperylene-3,4,9,10-tetracarboxylic dianhydride (II) can be carried out by filtering off the precipitated product, washing it with 85–88% by weight sulfuric acid, stirring it into water, filtering off the product again, washing it with water and then drying it.

Step a) of the novel three-stage preparation process, the reaction of 1,7-dibromoperylene-3,4,9,10-tetracarboxylic dianhydride (II) with the primary amine, is carried out in the presence of a polar aprotic solvent with or without an imidation catalyst.

Suitable polar aprotic solvents in this instance are, in particular, aprotic nitrogen heterocycles, such as pyridine, pyrimidine, quinoline, isoquinoline, quinaldine, N-methylpiperidine, N-methylpiperidone and, in particular, N-methylpyrrolidone.

The quantity of solvent used is not critical per se and is usually 5–20 kg, preferably 10–15 kg, per kg of (II).

Suitable imidation catalysts include organic and inorganic acids, for example formic acid, acetic acid, propionic acid and phosphoric acid, which are preferably employed in a highly concentrated form, and also organic and inorganic salts of transition metals such as zinc, iron and copper and of magnesium, examples being zinc acetate, zinc propionate, zinc oxide, iron(II) acetate, iron(III) chloride, iron(II) sulfate, copper(II) acetate, copper(II) oxide and magnesium acetate. Of course it is also possible to use mixtures of these catalysts.

The presence of an imidation catalyst is particularly advisable when reacting aromatic amines and is also advantageous when reacting cycloaliphatic amines, but is usually unnecessary when reacting, in particular, short-chain aliphatic amines.

When employed, the amount of catalyst is generally 5–80% by weight based on (II). Preferred amounts are 50–80% by weight for the organic acids and 10–40% by weight for the transition metal salts and magnesium salts, each based on (II).

Primary amines which can be employed in the novel preparation process are all those amines which are stable under reaction conditions and which when reacted with perylene-3,4,9,10-tetracarboxylic dianhydrides form diimides which can be hydrolyzed under basic conditions.

Examples of particularly preferred primary amines III are stearylamine, 5-nonylamine, cyclopentylamine, cyclohexylamine, cycloheptylamine, aniline, 4-methylaniline, 4-ethylaniline, 4-tert-butylaniline, 3,5-dimethylaniline, 3,5-diethylaniline and 3,5-di-tert-butylaniline.

The molar ratio of amine III to (II) is normally from about 2:1 to 4:1, preferably 2.2:1 to 3:1.

The reaction temperature in step a) is generally 40–180° C. For the reaction of aliphatic and cycloaliphatic amines it is preferably 60–100° C., and for aromatic amines preferably 120–160° C.

It is advisable to work under an inert-gas atmosphere (for example using nitrogen).

Step a) of the novel process can be carried out at atmospheric or superatmospheric pressure, usually up to 10 bar. Working under pressure is especially useful when using volatile amines (boiling point≦about 180° C.).

The reaction usually takes 2–10 hours, especially 4–7 hours.

The procedure in step a) is advantageously as follows:
1,7-Dibromoperylene-3,4,9,10-tetracarboxylic dianhydride (II), solvent and (if used) catalyst are charged to the reaction vessel, the amine III is added with stirring at room temperature, the apparatus is flushed with nitrogen for about 15 minutes, and the mixture is heated to the reaction temperature with stirring and held there for about 4–7 hours. After cooling to room temperature the reaction product is filtered off, washed with an aliphatic alcohol such as methanol and dried.

If the reaction is carried out under pressure the reactor used is a pressure apparatus to which a nitrogen pressure of about 1–2 bar is applied after introducing the components, which are then heated at the reaction temperature for the desired time and then cooled, after which the reactor is let down.

In general the 1,7-dibromoperylene-3,4,9,10-tetracarboxylic diimide IV obtained in step a) is already of such a purity (>95%) that it can be used directly for the subsequent reactions. Analytically pure products, with purities of >98%, can be prepared by dissolving the product in a halogenated hydrocarbon such as methylene chloride, chloroform or tetrachloroethane, filtering the solution over silica gel and concentrating the filtrate to dryness.

Step b) of the novel three-stage preparation process, the reaction of 1,7-dibromoperylene-3,4,9,10-tetracarboxylic diimide IV with the aromatic alcohol or thioalcohol V, is carried out in the presence of an inert aprotic solvent and a non-nucleophilic or weakly nucleophilic base.

Suitable inert aprotic solvents in this case are, in particular, nitrogen heterocycles such as pyridine, pyrimidine, quinoline, isoquinoline, quinaldine and, in particular, N-methylpyrrolidone.

The quantity of solvent used is not critical per se and is usually 10–50 kg, preferably 25–35 kg, per kg of diimide IV.

Particularly suitable bases are alkali metal hydroxides, for example sodium hydroxide and potassium hydroxide, and especially alkali metal carbonates, for example sodium carbonate and potassium carbonate, which are used in anhydrous form.

2–3, preferably 2.2–2.5, mole equivalents of base are generally employed per mole of diimide.

The reaction temperature in step b) is usually 60–180° C., in particular 80–140° C.

It is advisable to work under an inert-gas atmosphere (for example using nitrogen).

The molar ratio of aromatic alcohol or thioalcohol V to diimide IV is in general from 2:1 to 3:1, preferably from 2.0:1 to 2.2:1.

The reaction to form the perylimides VI is usually over after 1–5 hours, in particular 1–2 hours.

The procedure of step b) is advantageously as follows:
A stirred suspension of diimide IV, alcohol or thioalcohol V and base in the solvent is charged to the reaction vessel and is heated at the reaction temperature for 1–2 hours under nitrogen. The reaction mixture is cooled to room temperature and introduced into about 3 times the volume of a dilute inorganic acid, for example 5–10% by weight hydrochloric acid, and the precipitated reaction product is filtered off, washed with water until the washings are neutral, and dried under reduced pressure.

Once treated in this way, the perylimides VI are normally already of such a purity (>95%) that further purification is unnecessary. Analytically pure samples can be obtained by recrystallization from halogenated hydrocarbons, such as methylene chloride or chloroform, or by filtering a solution in these solvents over silica gel and then concentrating the filtrate.

Step c) of the novel three-stage preparation process, the hydrolysis of the perylimide VI to the dianhydride I, is carried out in the presence of a polar protic solvent and a base.

Particularly suitable polar protic solvents in this case are $C_1$–$C_{10}$-alkanols such as ethanol, propanol, n-butanol, tert-butanol, 2-methyl-2-butanol, n-hexanol, n-decanol and, preferably, isopropanol. To accelerate the hydrolysis reaction it is expedient to add water, generally 0.1–0.2 mol per mmol of perylimide VI.

The quantity of solvent employed is not critical per se and is usually 50–200 kg, preferably 60–80 kg, per kg of perylimide VI.

Particularly suitable bases are alkali metal hydroxides, such as sodium hydroxide and potassium hydroxide, of which generally 4–10 kg, preferably 5–7 kg, are employed per kg of perylimide VI.

The reaction temperature in stage c) is usually 20–140° C., in particular 40–90° C.

The hydrolysis is generally over after 3–10 hours, in particular 4–6 hours.

The procedure in step c) is expediently as follows:

A mixture of perylimide VI, solvent and base is heated at the desired reaction temperature for 4–6 hours and cooled to room temperature, where the precipitated crude product is filtered off and washed with an alcohol such as isopropanol or propanol until the washings are colorless. For further purification, the resulting dianhydride I is expediently introduced into 30–100 times the amount of dilute inorganic acid, for example 5–12% by weight hydrochloric acid, boiled up briefly, filtered off after cooling, washed to neutrality with water and dried.

In the single-stage process variant the 1,7-dibromoperylene-3,4,9,10-tetracarboxylic dianhydride (II) is reacted directly with the aromatic alcohol or thioalcohol V.

The reaction conditions, such as the nature and quantity of the solvent and base and the reaction temperature, correspond to those in step b) of the three-stage process. However, the molar ratio of V to (II) is generally from 2:1 to 10:1, preferably from 4:1 to 6:1. Moreover, longer reaction times of from 4 to 10 hours, in particular from 5 to 7 hours, are generally required.

The procedure for the single-stage variant is expediently as follows:

A stirred suspension of 1,7-dibromoperylene-3,4,9,10-tetracarboxylic dianhydride (II), alcohol or thioalcohol V and base in the solvent is charged to the reaction vessel and heated at the reaction temperature for 5–7 hours under nitrogen. After cooling to about 50° C., the precipitated reaction product is filtered off and washed with cold solvent. The solid is then stirred up in dilute inorganic acid, for example 5–10% by weight hydrochloric acid, then the liquid phase is removed by decanting, the residue is made up with hot water and stirred for about 30 minutes at 80–85° C., and then the solid product is filtered off, preferably while still hot, washed with hot water until the washings are neutral, and dried under reduced pressure.

The products obtained in this way generally contain about 10–15% contamination with unreacted, or only partially reacted, starting material (II), and consequently it is advisable to purify them further, for example by fractional crystallization in an appropriate high-boiling solvent such as N-methylpyrrolidone or tetrachloroethane, or by filtering a solution of the crude product in these solvents over a short silica-gel column.

Using the novel preparation processes (including subsequent purification in the case of the single-stage variant) it is possible to obtain the 1,7-disubstituted perylene-3,4,9,10-tetracarboxylic dianhydrides I in a procedurally simple and economic manner and in high purities (generally>95%) and good yields (generally>70% in the three-stage process and >55% in the single-stage process).

The novel dianhydrides I are advantageously suitable for pigmenting printing inks, coating compositions, especially daylight-fluorescent colors, and plastics, as laser dyes and as precursors for the preparation of fluorescent dyes, polymeric colorants, pigments and pigment additives.

The novel perylimides VI can also be used with advantage as pigments and dyes for coloring high molecular mass organic materials and inorganic materials, as laser dyes and as organic materials for electroluminescence applications.

EXAMPLES

A) Preparation of 1,7-dibromoperylene-3,4,9,10-tetracarboxylic dianhydride (II)

Example 1

A mixture of 292.5 g (0.75 mol) of perylene-3,4,9,10-tetracarboxylic dianhydride (purity>98%) and 4420 g of 100% by weight sulfuric acid was stirred for 12 hours at room temperature, 7 g of iodine were added, and the mixture was then heated to 85° C. 262.5 g (1.64 mol) of bromine were then added dropwise over 8 hours.

The reaction mixture was cooled to room temperature, the excess bromine was displaced by nitrogen, and the concentration of sulfuric acid in the reaction mixture was reduced to 86% by weight by adding, a little at a time, a total of 670 g of water over 1 hour. The reaction mixture, which heats up to 85° C. during this procedure, was cooled to room temperature and the precipitated product was filtered off over a G4 glass frit, washed with 3 kg of 85% by weight sulfuric acid, then stirred up in 5 l of water, filtered off again, washed to neutrality and dried under reduced pressure at 120° C.

370 g of II were obtained in the form of a bright red, finely crystalline powder with a melting point>360° C. and a purity of >98%, corresponding to a yield of 90%.

Analytical data:

Elemental analysis (% by weight calc./found): C: 52.4/52.1; H: 1.1/1.1; O: 17.45/17.4; Br: 29.1/29.4; IR (KBr): $v$=1782+1770 (s, C=O), 1735+1723 (s, C=O) $cm^{-1}$; UV/VIS ($H_2SO_4$): $\lambda_{max}$ ($\epsilon$)=408 (10309), 520 (29410), 554 (43141) nm.

B1) Preparation of 1,7-diaroxy-substituted perylene-3,4,9,10-tetracarboxylic dianhydrides I in Accordance with the Three-stage Process Variant a) Preparation of 1,7-dibromoperylene-3,4,9,10-tetracarboxylic diimides (IV)

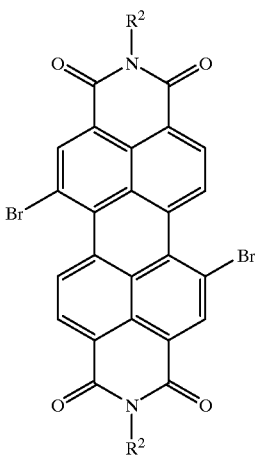

IV

Examples 2 to 4

First a g of imidation catalyst and then, a little at a time, a total of 381 mmol (280 mmol) in Example 3) of the amine $R_2$-$NH_2$ (III) were added with stirring to a mixture of 69.9 g (127 mmol) of 1,7-dibromoperylene-3,4,9,10-tetracarboxylic dianhydride (II) from Example 1 in 900 ml of N-methyl-2-pyrrolidone. The reaction mixture was then heated to T° C. under nitrogen and stirred at this temperature for 6 hours.

After cooling to room temperature, the precipitated reaction product was filtered off, washed with a total of 2 l of methanol and dried under reduced pressure at 100° C.

Further details regarding these experiments and their results are compiled in Table 1.

Analytical data for Example 4: Elemental analysis (% by weight calc./found): C: 63.5/63.2; H: 3.2/3.25; N: 3.7/3.7; O: 8.5/8.7; Br: 21.1/21.0; mass (FD): m/z=754 (M$^+$, 100%); IR (KBr): ν=1696 (s, C=O), 1653 (s, C=O) cm$^{-1}$; UV/VIS (CHCl$_3$): $\lambda_{max}$ (ε)=485 (28570), 532 (44201) nm.

b) Preparation of 1,7-diaroxy-substituted perylene-3,4,9,10-tetracarboxylic diimides VI

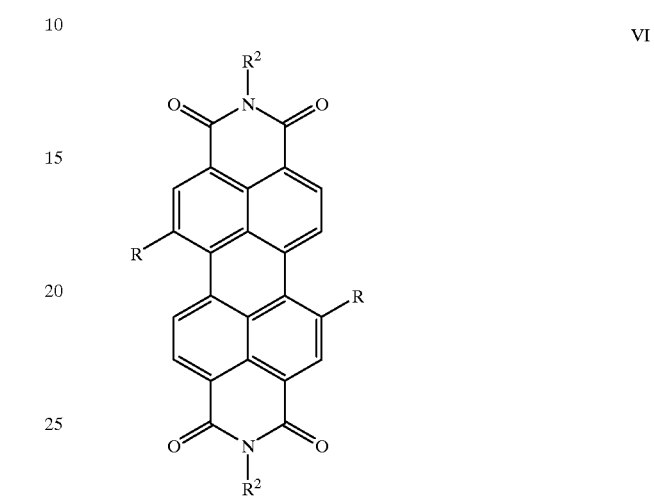

Examples 5 to 7

20 mmol each of the 1,7-dibromoperylene-3,4,9,10-tetracarboxylic diimide (IV) from Examples 2 and 4, respectively, were introduced with stirring into 450 ml of N-methylpyrrolidone, then 6.4 g (46 mmol) of anhydrous potassium carbonate and a g (40 mmol) of the hydroxy-aromatic compound V were added in succession, and the mixture was heated at 120° C. under nitrogen for 1.5 h.

After cooling to room temperature, the reaction mixture was introduced with stirring into 1.5 l of 6% by weight

TABLE 1

| | | | | | Result | | | |
|---|---|---|---|---|---|---|---|---|
| Ex. | $R_2$ | a g | Imidation catalyst | T[° C.] | Yield [g]/[%] | Purity [%] | Appearance | m.p. [° C.] |
| 2 | Cyclohexyl | 42.8 | Acetic acid | 85 | 75.1/83 | 97 | bright red, microcrystalline | >360 |
| 3 | Cyclohexyl | 21.0 | Zinc acetate | 100 | 73.9/82 | 97 | bright red, microcrystalline | >360 |
| 4 | 3,5-Dimethyl-phenyl | 17.5 | Zinc acetate | 140 | 83.8/87 | 96 | dark red, microcrystalline | >360 |

Analytical data for Examples 2 and 3: Elemental analysis (% by weight calc./found): C: 60.7/60.6; H: 4.0/4.0; N: 3.9/3.9; O: 9.0/9.0; Br: 22.4/22.3; IR (KBr): ν=1698 (s, C=O), 1655 (s, C=O cm$^{-1}$; UV/VIS (CHCl$_3$): $\lambda_{max}$ (ε)= 491 (33411), 526 (50033) nm.

hydrochloric acid. The precipitated reaction product was filtered off, washed to neutrality with water, and dried under reduced pressure at 100° C.

Further details regarding these experiments, and their results, are compiled in Table 2.

TABLE 2

| Ex. | R² | R | Diimide IV from Ex. | a g | Hydroxy-aromatic compound V | Yield [g]/[%] | Purity [%] | Appearance | m.p. [° C.] |
|---|---|---|---|---|---|---|---|---|---|
| 5 | Cyclohexyl | Phenoxy | 2 | 3.8 | Phenol | 14.5/98 | 93 | dark red, crystalline | >360 |
| 6 | Cyclohexyl | p-tert-Butylphenoxy | 2 | 6.0 | p-tert-Butylphenol | 16.0/94 | 95 | magenta, micro-cristalline | >360 |
| 7 | 3,5-Dimethylphenyl | p-tert-Butylphenoxy | 4 | 6.0 | p-tert-Butylphenol | 17.7/93 | 94 | dark red, microcristalline | >360 |

Analytical data for Example 5: Elemental analysis (% by weight calc./found): C: 78.0/77.5; H: 5.2/5.3; N: 3.8/3.7; O: 13.0/13.4; mass (FD): m/z=738 (M⁺, 100%); IR (KBr): ν=1695 (s, C=O), 1654 (s, C=O) cm⁻¹; UV/VIS (CHCl₃): $\lambda_{max}$ (ε)=401 (7455), 513 (37102), 549 (55004) nm.

Analytical data for Example 6: Elemental analysis (% by weight calc./found): C: 79.0/78.8; H: 6.4/6.4; N: 3.3/3.2; O: 11.3/11.4; mass (FD): m/z=850 (M⁺, 100 %); IR (KBr): ν=1697 (s, C=O), 1654 (s, C=O) cm⁻¹; UV/VIS (CHCl₃): $\lambda_{max}$ (ε)=404 (9447), 512 (34785), 547 (52117) nm.

Analytical data for Example 7: Elemental analysis (% by weight calc./found): C: 80.5/80.4; H: 5.6/5.6; N: 3.1/3.1; O: 10.7/10.8; mass (FD): m/z=894 (M⁺, 100%); IR (KBr): ν=1699 (s, C=O), 1651 (s, C=O) cm⁻¹; UV/VIS (CHCl₃): $\lambda_{max}$ (ε)=408 (10703), 511 (32187), 544 (58330) nm.

Example 7, respectively, 1 l of isopropanol, 65 g of potassium hydroxide and 26 g of water was refluxed for 5 hours.

After cooling to room temperature the precipitated reaction product was filtered off, washed with isopropanol until the washings were colorless, then introduced with stirring into 1 l of 10% by weight hydrochloric acid and heated briefly to boiling point. After cooling to room temperature, the product was again filtered off, washed to neutrality with water and dried under reduced pressure at 100° C.

Further details regarding these experiments and their results are compiled in Table 3. The purity of the products was determined by UV/VIS spectroscopy and semiquantitative thin-layer chromatography on silica gel using trichloroacetic acid/toluene as the mobile phase.

TABLE 3

| Ex. | R | Diimide VI from Ex. | Yield [g]/[%] | Purity [%] | Appearance | m.p. [° C.] |
|---|---|---|---|---|---|---|
| 8 | Phenoxy | 5 | 7.4/94 | 98 | red-violet, microcrystalline | >360 |
| 9 | p-tert-Butylphenoxy | 6 | 7.7/95 | 98 | red-violet, amorphous | >360 |
| 10 | p-tert-Butylphenoxy | 7 | 7.3/91 | 96 | red-violet, amorphous | >360 | c) Preparation of 1,7-diaroxy-substituted perylene-3,4,9,10-tetracarboxylic dianhydrides I

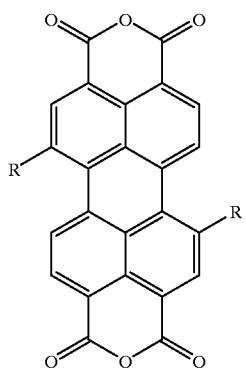

Examples 8 and 10

A mixture of 10 g of the 1,7-diaroxy-perylene-3,4,9,10-tetracarboxylic diimide (VI) from each of Example 5, 6 and Analytical data for Example 8: Elemental analysis (% by weight calc./found): C: 75.0/74.8; H: 2.8/2.8; O: 22.2/22.3; IR (KBr): ν=1758 (s, C=O), 1729 (s, C=O) cm⁻¹; UV/VIS (H₂SO₄): $\lambda_{max}$ (ε)=415 (8832), 559 (38103) nm.

Analytical data for Example 9 and 10: Elemental analysis (% by weight calc./found): C: 76.7/76.6; H: 4.7/4.7; O: 18.6/18.7; IR (KBr): ν=1755 (s, C=O), 1730 (s, C=O); UV/VIS (H₂SO₄): $\lambda_{max}$ (ε)=412 (9405), 561 (32746) nm.

B2) Preparation of 1,7-di(p-tert-butylphenoxy) perylene-3,4,9,10-tetracarboxylic dianhydride (I') in Accordance with the Single-stage Process Variant Example 11

First, 8.3 g (60 mmol) of anhydrous potassium carbonate and then 13.65 g (91 mmol) of p-tert-butylphenol were added with stirring to a suspension of 10 g (18.2 mmol) of 1,7-dibromoperylene-3,4,9,10-tetracarboxylic dianhydride (II) (Example 1) in 320 ml of N-methylpyrrolidone. The reaction mixture was then heated to 120° C. under nitrogen and stirred at this temperature for 6 hours.

After cooling to 50° C., the precipitated reaction product was filtered off, washed with hot (50° C.)

N-methylpyrrolidone and then stirred up briefly in 500 ml of 6% by weight hydrochloric acid. After the supernatant solution had been removed by decanting, the solid which remained was admixed with 600 ml of water and the mixture was heated at 80–85° C. with stirring for 0.5 hours. The product was filtered off while hot, washed to neutrality with hot water and dried under reduced pressure at 120° C.

8.6 g of I' were obtained as a red-violet powder with a melting point >360° C. and a purity of 90%, corresponding to a yield of 63%.

Example 11a

For purification, 10 g of 1,7-di(p-tert-butylphenoxy)-perylene-3,4,9,10-tetracarboxylic dianhydride (I') obtained according to Example 11 were stirred in 2 l of N-methylpyrrolidone for 1 hour. This mixture was subsequently filtered over a 2 l G4 glass frit which was filled to ⅔ of its capacity with silica gel (N-methylpyrrolidone as mobile phase).

After evaporating off the N-methylpyrrolidone under reduced pressure, the filtrate yielded 8.1 g of I' as a red-violet, crystalline powder with a purity >98%, whose analytical data correspond to those indicated for Example 9.

We claim:

1. A 1,7-disubstituted perylene-3,4,9,10-tetracarboxylic diimide of the general formula VI:

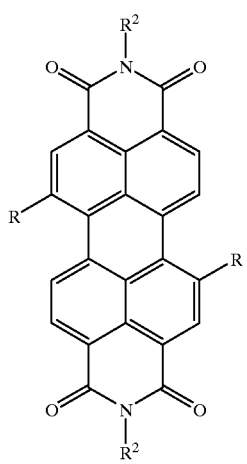

where
R is aryloxy, arylthio, hetaryloxy or hetarylthio each of which can be substituted one or more times by $C_1$–$C_{30}$-alkyl whose carbon chain can be interrupted by one or more groups —O—, —S—, $NR^1$—, —CO— and/or —$SO_2$— and/or can be substituted one or more times by —$COOR^1$, —$SO_3R^1$, hydroxyl, cyano, $C_1$–$C_6$-alkoxy, $C_5$–$C_8$-cycloalkyl or a 5- to 7-membered heterocyclic radical which is attached via nitrogen and can contain further heteroatoms, or can be substituted one or more times by $C_1$–$C_6$-alkoxy, cyano, —$COOR^1$ or —$SO_3R^1$, where $R^1$ is hydrogen or $C_1$–$C_6$-alkyl, and
$R^2$ is $C_4$–$C_{30}$-alkyl whose carbon chain can be interrupted by one or more groups —O—, —S— or —CO—, or is $C_5$–$C_8$-cycloalkyl or aryl which can be substituted one or more times by a $C_1$–$C_6$-alkyl or a $C_1$–$C_6$-alkoxy.

2. A compound of the general formula VI as set forth in claim 1, where:

R is aryloxy or hetaryloxy each of which can be substituted one or more times by $C_1$–$C_{18}$-alkyl, —$COOR^1$, —$SO_3R^1$ or $C_1$–$C_6$-alkoxy; and $R^2$ is $C_5$–$C_8$-cycloalkyl or phenyl which can be substituted in the meta and/or para positions by $C_1$–$C_6$-alkyl or $C_1$–$C_6$-alkoxy.

3. A process for the preparation of a compound of formula VI as claimed in claim 1, which comprises a) reacting 1,7-dibromoperylene-3,4,9,10-tetracarboxylic dianhydride or 1,7-dibromoperylene-3,4,9,10-tetracarboxylic acid in the presence of a polar aprotic solvent and in the presence or absence of an imidation catalyst, with a primary amine of the general formula III:

$R^2$—$NH_2$      III and b) reacting the 1,7-dibromoperylene-3,4,9,10-tetracarboxylic diimides, formed in step a), of the general formula IV:

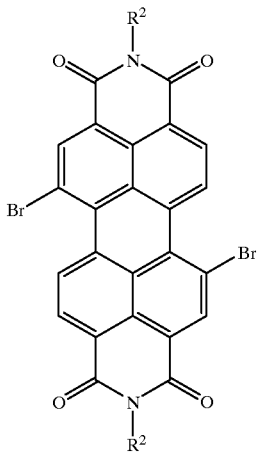

in the presence of an inert aprotic solvent and of a non-nucleophilic or only weakly nucleophilic base with an aromatic alcohol or thioalcohol of the general formula V:

H—R      V.

4. A method for coloring a high molecular mass material comprising:

incorporating a compound of formula VI into said material as a dye or a pigment or contacting said material with a compound of formula VI thereby coloring said material.

5. A laser dye or organic material for an electroluminescent application comprising a compound of formula VI.

6. A method for coloring a high molecular mass material comprising contacting said material with a means for dyeing or pigmenting wherein said means comprises a compound of formula VI.

* * * * *